United States Patent [19]

Matkan et al.

[11] Patent Number: 4,681,806
[45] Date of Patent: Jul. 21, 1987

[54] PARTICLES CONTAINING RELEASABLE FILL MATERIAL AND METHOD OF MAKING SAME

[75] Inventors: Josef Matkan, Malvern; Richard J. Treleaven, Toorak Gardens, both of Australia

[73] Assignee: Minnesota Mining and Manufacturing Company, St. Paul, Minn.

[21] Appl. No.: 829,005

[22] Filed: Feb. 13, 1986

[51] Int. Cl.⁴ ............ A01N 25/28; B01J 13/02; C08G 18/82

[52] U.S. Cl. .................. 428/402.21; 71/3; 71/64.13; 71/70; 71/71; 264/4.3; 264/4.33; 264/4.7; 424/DIG. 10; 424/409; 427/150; 427/213.32; 427/213.33; 428/321.5; 428/423.3; 514/788; 514/962; 514/965

[58] Field of Search .............. 71/3, 64.13, 70, 71; 264/4.3, 4.7; 424/32, DIG. 10; 427/213.32, 213.33; 428/321.5, 402.21, 423.3; 514/788, 962, 965

[56] References Cited

U.S. PATENT DOCUMENTS

| | | | |
|---|---|---|---|
| 3,016,308 | 1/1962 | Macaulay | 117/36.7 |
| 3,429,827 | 2/1969 | Ruus | 252/316 |
| 3,575,882 | 4/1971 | Vandegaer et al. | 252/316 |
| 3,577,515 | 5/1971 | Vandegaer | 424/32 |
| 3,578,605 | 5/1971 | Baxter | 252/316 |
| 3,796,669 | 3/1974 | Kiritani et al. | 252/316 |
| 4,046,741 | 9/1977 | Scher | 264/4.7 |
| 4,076,774 | 2/1978 | Short | 264/4 |
| 4,138,362 | 2/1979 | Vassiliades | 428/402.21 |
| 4,140,516 | 2/1979 | Scher | 264/4.7 |
| 4,209,188 | 6/1980 | Chao et al. | 282/27.5 |
| 4,285,720 | 8/1981 | Scher | 264/4.7 |
| 4,305,838 | 12/1981 | Iwasaki et al. | 252/316 |
| 4,308,165 | 12/1981 | Vassiliades et al. | 428/402.21 |
| 4,404,251 | 9/1983 | Jabs et al. | 428/320.6 |
| 4,417,916 | 11/1983 | Beestman et al. | 71/93 |
| 4,423,091 | 12/1983 | Iwasaki et al. | 427/213.34 |
| 4,428,978 | 1/1984 | Jabs et al. | 427/150 |
| 4,428,983 | 1/1984 | Nehen et al. | 428/402.21 |
| 4,456,569 | 6/1984 | Rodson et al. | 264/4.7 |
| 4,636,451 | 1/1987 | Matkin et al. | 430/409 |

FOREIGN PATENT DOCUMENTS 1371179 10/1974 United Kingdom .
1396543 6/1975 United Kingdom .

*Primary Examiner*—James C. Cannon
*Attorney, Agent, or Firm*—Donald M. Sell; James A. Smith; David L. Weinstein

[57] ABSTRACT

Particles containing a releasable fill material and method of preparing same. A particle comprises a continuous polyurea surface layer, and an interior portion comprising a polyurea matrix, said matrix having a fill material contained therein, said matrix forming a continuum extending from the surface layer into the interior of the particle. The particles can be prepared by a method comprising:
(1) admixing fill material, an isocyanate, and a matrix-forming co-reactant to form a mixture,
(2) emulsifying said mixture in an aqueous medium containing a non-reactive emulsifying agent to provide a dispersion of spheres, and
(3) hydrolyzing a first portion of the isocyanate near the surface of said spheres to initiate formation of polyurea at the surface of said spheres as a thin, substantially continuous layer and in the interiors of the spheres as a continuum for some distance beneath the surface of the spheres, and reacting a second portion of the isocyanate within said spheres with said matrix-forming co-reactant to form additional matrix material in the interior of the spheres.

12 Claims, No Drawings

PARTICLES CONTAINING RELEASABLE FILL MATERIAL AND METHOD OF MAKING SAME

BACKGROUND OF THE INVENTION

This invention relates to spheres which are totally enclosed by a layer and contain within a matrix fill material for controlled release or pressure release and a method of producing same.

The use of microspheres for the controlled release or pressure release of liquid or liquefiable fill materials is well known in a variety of chemical fields. In agriculture, controlled release techniques are used to improve the efficiency of herbicides, insecticides, fertilizers, fungicides, and bactericides. Non-agricultural applications of controlled or pressure release include containment of dyes, dye precursors, adhesives, inks, flavoring agents, fragrances, and pharmaceuticals.

Fill materials for controlled release or pressure release can be contained in particles of many known forms, such as, microcapsules or droplets of liquids or semi-fluids contained within a shell or coating, solids, solid/liquid mixtures, and aggregates of solid particles which are coated or contained within a shell or coating. In some instances the coating or shell is porous and the fill material is released into the surrounding medium by slow diffusion through the pores. Alternatively, the coating or shell may be soluble in water or some other suitable solvent allowing release of the fill material upon contact with such solvent. In other instances the coating or shell is ruptured by external pressure or force to release the fill material.

One of the disadvantages of such prior art methods of containing fill materials is the difficulty of precisely controlling the release of the contained substance. If the coating or shell is of the porous kind, release of the fill material may occur before the microcapsule or coated particle is placed in the environment into which its release is required. In other instances in which non-porous coatings or shells are used, it is generally necessary to ensure that the shell or coating is of substantial thickness to prevent premature release of the fill material by accidental rupture of the shell or coating, for instance, during handling, particularly when such fill material is a liquid of relatively low viscosity.

SUMMARY OF THE INVENTION

In accordance with the present invention there is provided a novel method of producing spheres containing solid or liquid fill material within a matrix surrounded by a surface layer which is a continuum of said matrix whereby the above listed disadvantages of the prior art are overcome.

The composition for the formation of spheres initially comprises the selected fill material for controlled release, a reactive isocyanate, and a matrix-forminq co-reactant, e.g. a drying or semi-drying vegetable oil. If the fill material is a solid, it is first dissolved or dispersed in a suitable oleophilic liquid. This composition is emulsified in an aqueous phase to form spherical droplets therein, generally in the size range 1 to 1000 microns, depending on the requirement of the particular application. The reactive isocyanate at the surface of the spherical droplets hydrolyses upon contact with the aqueous phase and initiates formation of polyurea which is at high concentration at the surface of such spheres as a very thin yet substantially continuous layer and decreases in concentration as it diffuses into the spheres for some distance beneath the surface thereof. The remainder of the isocyanate reacts with the matrix-forming co-reactant to substantially solidify the co-reactant to form a porous matrix within and throughout the spheres. The selected fill material is contained within such porous matrix, and the matrix supports the thin surface layer as a continuum thereof in such manner that the substantially spherical shape is retained during normal handling, and premature release of the fill material through the thin surface layer does not occur. Depending on the application, the thus formed spheres can be used as a dispersion or suspension in the aqueous phase or can be removed form the aqueous phase and used in dry form.

DETAILED DESCRIPTION OF THE INVENTION

A detailed description will now be given of the method of preparing spheres containing fill material for controlled release or pressure release in accordance with this invention. As used herein; the terms "spheres" and "spherical" are also intended to include the terms spheroid and spheroidal.

The fill material and solvent therefor, if required, vegetable oil, isocyanate, and optional additives are normally compounded in such proportions that they form the sphere-forming composition with a viscosity generally within the range 20-50,000 centipoise at the chosen emulsification temperatures, the viscosity being selected primarily to allow the chosen emulsification method and emulsifying agent to produce spherical droplets or particles in suspension in the desired particle size range, which may be within the range of 1 to 1000 microns, depending on the particular application.

In those instances in which the fill material contains a solid such as an agricultural chemical, dye precursor, dye, adhesive or the like, such required component is dissolved in a suitable solvent at the required concentration, following which the vegetable oil is added and blended therewith by stirring. The use of a high shear mixer, such as a Cowles dissolver, may be advantageous if insoluble solids such as pigments are included in the fill material. To form the sphere-forming composition, the isocyanate is added to the above mixture and blended therewith by stirring immediately prior to emulsification, which can be carried out at ambient temperatures or at elevated temperatures if desired. The milled or homogenized mixture is placed in a suitable container and heated, if required, to a temperature no greater than 70° C., and the isocyanate at ambient temperature is then added and blended in with a high speed stirrer. The thus-formed sphere-forming composition is then introduced into the aqueous solution of the emulsifying agent which is preferably at about the same temperature as the blend.

The mixture comprising the fill material or the solution thereof, isocyanate, matrix-forming co-reactant, optional drier and catalyst, is emulsified at appropriate temperature to form a dispersion of spheres in an aqueous solution of an emulsifying agent.

Emulsification of the sphere-forming composition is carried out in an aqueous solution of an emulsifying agent, which is selected to be non-reactive or substantially non-reactive with isocyanates, that is to say, its rate of reaction with isocyanate should be considerably lower than the rate of isocyanate hydrolysis by contact with water. Suitable emulsifying agents include sodium, potassium and ammonium lignin sulphonates, ethylene maleic anhydride, sodium dodecylbenzene sulphonate, sodium salt of styrene maleic anhydride, and the like.

The emulsifying equipment can be of the batch type or the in-line or continuous type. Batch type equipment suitable for this purpose can be, for instance, the well-known Waring blender or like equipment of the high shear type. The equipment, however, should be so chosen that the actual emulsion-forming process, that is to say, the addition and admixing of the isocyanate to form the sphere-forming composition, the addition of the sphere-forming composition to the aqueous phase, and the time during which high shear force are applied for dispersion, is kept as short as possible, thus preventing the breakage of partially formed surface layers.

Upon formation of the dispersion of spheres in the aqueous solution of the emulsifying agent, that part of the isocyanate which is nearest the surface of the spheres is hydrolyzed by contact with water, whereby urea formation is initiated, such urea further reacting with the free isocyanate to form polyurea. Whilst the concentration of such polyurea is highest at the sphere surface where direct contact between isocyanate and water occurs, polyurea formation continues after initiation at the surface for some distance therebeneath into the sphere material. As the result of this, the polyurea at highest concentration present at the sphere surface forms a very thin, yet substantially continuous layer, and extends in a diffused or discontinuous form at decreasing concentration for some distance into the sphere. The remainder of the isocyanate, that is, non-reacted isocyanate just beneath the sphere surface in the zone containing diffused polyurea and the isocyanate in the body of the sphere, reacts with the matrix-forming co-reactant, generally forming a reaction product of the acylurea type when the co-reactant is vegetable oil to thereby substantially solidify the matrix-forming co-reactant in the form of a matrix or porous structure extending throughout the spheres and being sealed off by its continuum, that is, the thin yet substantially continuous polyurea surface layer. The fill material is contained within such porous matrix.

The formation of the surface layer and of the matrix may commence simultaneously during the emulsifying process, and, preferably, should be completed within a period of about 4 hours thereafter, depending on the materials chosen. In certain instances, the matrix formation, that is to say, the reaction between the isocyanate and the matrix-forming co-reactant may be only partially completed during such period, and full polymerization may occur during subsequent drying of the spheres at elevated temperatures. In any case, during such period, the emulsion is kept agitated or stirred at slow speed. This results in a dispersion in the aqueous solution of the emulsifying agent of spheres having a polyurea surface layer and containing a porous matrix with fill material.

Subsequent processing depends on the end use of the spheres. In agricultural applications, the dispersion may be used directly without further treatment or, alternatively, the emulsifying agent may be removed by washing if desired. Such removal is preferably carried out by centrifugal separation followed by washing with water and further centrifugal separation, if desired, or more simply by repeated decant washing. When the spheres contain a dye precursor suitable for the so-called carbonless paper manifold copying processes, it may be advantageous to incorporate a film-forming binder into the dispersion, with or without removal of the emulsifying agent, to enable the spheres to be coated onto paper and adhered thereto. Suitable binders include carboxy methyl cellulose, polyvinyl alcohol, sodium polyacrylate, and the like. Such binders should be of the type which can be rendered water insoluble prior to coating or of the type which become water insoluble by self-crosslinking or other mechanisms after coatings produced therefrom are dried. If the spheres are required to be in the form of a dry powder, the emulsifying agent is preferably removed as hereinbefore described, following which the remaining water can be removed by spray drying, filtration followed by air drying, vacuum evaporation, centrifugal separation followed by forced or natural evaporation, or other means, as desired.

Typical fill materials which can be contained in the microspheres of this invention for controlled release or pressure release include the following:

(1) Insecticides such as O-ethyl S-phenyl ethylphosphonedithiodate; ethyl 4,4'-dichlorobenzilate; 0,0-diethyl 0,2-ethylthioethyl phosphorothioate; S-1, 2-di(ethoxycarbonyl) ethyl 0,0-dimethyl phosphorodithioate; 0,0-diethyl 0-(2-isopropyl-4-methyl-6-pyrimidinyl) phosphorothioate;

(2) Defoliants such as tributyl phosphorotrithioite;

(3) Fungicides such as copper naphthenates;

(4) Insect repellants such as dibutyl phthalate; dibutyl succinate and N,N-diethyl-m-toluamide;

(5) Herbicides such as S-ethyl diisobutylcarbamate; S-ethyl di-propylthiocarbamate; N-butoxymethyl--chloro- 2',6'-diethylacetanilide; 2-sec-butyl-4,6-dinitrophenol;

(6) Dye precursors suitable for manifold copying such as crystal violet lactone; benzoyl leuco methylene blue; 4,4'-bis-dimethylaminobenzhydryl benzyl ether; rhodamine aniline lactam; p-nitrobenzyl leuco methylene blue; 3-methyl-spiro-dinaphthopyran.

Other fill materials which may be contained in the microspheres of the present invention include oil soluble dyes such as CI Solvent Red 2, CI Solvent Brown 3, CI Solvent Black 3, CI Solvent Blue 7 and CI Solvent Yellow 16, perfume oils, adhesives, and the like.

In carrying out the invention, the composition for the formation of spheres is prepared by admixing the selected fill material with a drying or semi-drying type vegetable oil and a reactive isocyanate. In those instances where the fill material is a solid it is firstly dissolved in a suitable solvent and such solution is then admixed with the vegetable oil and the isocyanate.

The solvent for the fill material must be of a type which does not dissolve or degrade in any way the polyurea surface layer of the spheres or the porous matrix structure contained within them, which is of acyl urea type as will be disclosed in more detail below. Suitable solvents for the fill materials include alkyl naphthalene, aromatic, aliphatic and isoparaffinic hydrocarbons, tetrahydronaphthalene, kerosene, amyl alcohol, ethyl amyl ketone, oxitol acetate, amyl acetate, cyclohexanone, dibutyl phthalate, dioctyl phthalate, and the like. Such solvents should be of the high boiling type in those instances in which it is required to dry the spheres at elevated temperatures, for instance, by spray drying to prepare dry powders therefrom. In those instances in which the sphere material remains in an aqueous dispersion for subsequent processing or application, lower boiling point solvents of substantially the same generic chemical types which are compatible with the specific fill material may be used.

The matrix-forming co-reactant is preferably a drying or semi-drying vegetable oil which is admixed with the fill material or the solution thereof serves the purpose of forming a matrix or porous structure within the spheres which contains the liquid fill material by substantially solidifying by reaction with the isocyanate. Suitable vegetable oils are the drying oils such as linseed, tung, oiticica and dehydrated castor oils, and the semi-drying oils such as safflower and sunflower oils. Metallic driers such as the naphthenates or octoates of lead, cobalt, and manganese may also be included to assist polymerization of the vegetable oil. Mixtures of oils can be used if desired.

The preferred isocyanates are tolylene diisocyanate, 4,4'-diphenylmethane diisocyanate, and polymethylene polyphenylisocyanate, but any aromatic or aliphatic polyfunctional isocyanates, such as diisocyanates, triisocyantes, tetraisocyanates, and isocyanate prepolymers can be used if desired. Catalysts such as tertiary amines, organometallic compounds, tertiary phosphine, alkali metal compounds, and radical forming agents may also be included if desired.

It is pointed out here that the novel and functionally essential feature of this invention is the provision of spheres containing such porous matrix structure and a thin yet substantially continuous surface sealing layer as a continuum thereof, because the porous matrix serves not only the purpose of containing the fill material but also the purpose of supporting the thin surface layer in such manner that the substantially spherical shape of the spheres is retained even after drying thereof, and during subsequent handling or processing of such spheres, no premature release of the fill material through the thus supported thin surface sealing layer occurs due to leakage or accidental damage or rupture.

Thus, in preparing microspheres in accordance with this invention, it is essential to ensure that both formulation and method allow the formation of thin surface layer as well as of a porous matrix throughout the spheres. This can be accomplished if the rate of reaction between the matrix-forming co-reactant, or mixture thereof with or without driers, and the isocyanate, or mixture thereof with or without catalysts, commences substantially simultaneously with hydrolysis of the isocyanate at the sphere surface which results from contact with the aqueous phase upon formation an emulsion of droplets of the sphere-forming composition. If the rate of reaction between the matrix-forming co-reactant and the isocyanate is significantly slower than the rate of hydrolysis or if such reaction commences some considerable time after commencement of hydrolysis, much of the isocyanate may migrate towards the surface of the sphere rather than polymerizing in situ by reaction with the co-reactant to form a matrix. This would result in a surface layer of excessive thickness, impaired release properties, and irregular shape of particles, particularly upon drying. It will be realized that the rate of reaction between the matrix-forming co-reactant and the isocyanate and the rate of hydrolysis depend not only on the selection of the reactive materials and catalysts, but, as disclosed below, also on the viscosity of the sphere-forming composition, nature of the aqueous phase, temperature and speed of emulsification, as well as type of emulsifier employed.

The polyurea surface layer, being a continuum of said matrix, may be described functionally as a sealing or isolation or barrier or protective layer. The thickness and/or strength of such surface layer, the distance beneath the sphere surface to which the zone containing both diffused polyurea and isocyanate/matrix-forming co-reactant reaction product extends, and the final hardness of the spheres are governed largely by the type and quantity of isocyanate, type and quantity of matrix-forming co-reactant, viscosity of liquid fill material, and presence or absence of driers or catalysts. It will be realized that isocyanates such as tolylene diisocyanate and 4,4'-diphenylmethane diisocyanate hydrolyze more rapidly in the presence of water than, for example, polymethylene polyphenylisocyanate. Thus it could be expected that the first two of these materials will hydrolyze very quickly on contact with water to initiate the polyurea forming reaction to produce the surface layer. With polymethylene polyphenylisocyanate, hydrolysis will occur at a somewhat slower rate. It can also be expected that proportionally more of the fast hydrolyzing isocyanate will react to form the surface layer than will be the case with slower hydrolyzing isocyanates. Therefore, with fast hydrolyzing isocyanates it is necessary to include catalysts in order that the reaction with the vegetable oil may commence substantially simultaneously with hydrolysis; otherwise a weak matrix formation may result, particularly if the composition for formation of spheres is of relatively low viscosity, allowing high migration mobility of the isocyanate. With a vegetable oil of the drying type, such as linseed oil, which is susceptible to oxidation polymerization as well as reacting with isocyanate, it is possible to produce spheres in which the matrix is virtually solid when finally dried. However, with a semi-drying oil, such as safflower oil or sunflower seed oil, oxidation polymerization may be diminished to the extent that the matrix within the spheres retains some degree of softness or plasticity. Thus, the reactive components can be balanced in proportion and chosen in type to produce, within limits, whatever surface layer thickness is desired.

It will be realized from the foregoing that the type and quantity of matrix-forming co-reactant and the type and quantity of isocyanate included therewith prior to emulsification will have a significant influence on matrix formation. The relatively slow polyurea formation by hydrolysis-initiated polymerization of isocyanate allows time for reaction of part of the isocyanate with the matrix-forming co-reactant. In contrast, the use of a second reactant such as an amine in the aqueous phase would accelerate considerably the formation of the polyurea surface layer at the time at which the matrix-forming co-reactant is still relatively fluid, which would cause isocyanate migration towards the outer surface, resulting in isocyanate depletion within the particles, such depletion in the limiting case precluding matrix formation with the matrix-forming co-reactant. The use of such second reactant is therefore not desirable in accordance with this invention.

The quantity of matrix-forming co-reactant added for matrix formation should be at least sufficient to allow the formation of a matrix of adequate strength to support the thin outer surface layer. For this purpose the matrix-forming co-reactant should comprise a minimum of about 5 percent of the fill material. The maximum content of such matrix-forming co-reactant is governed by the necessity to obtain release of the fill material under selected conditions. Consequently, the matrix-forming co-reactant should not comprise more than about 20 percent of the fill material, the preferred range being 6 percent to 10 percent.

The following Examples will serve to further illustrate the present invention.

EXAMPLE 1

A blend was prepared comprising the following:
Crystal violet lactone: 2.5 grams
Benzoyl leucomethylene blue: 0.5 grams
Dibutyl phthalate: 80 grams
Safflower oil: 20 grams The fill material comprising the dye precursors crystal violet lactone and benzoyl leucomethylene blue dissolved in the dibutyl phthalate, following which the safflower oil was added and the mixture homogenized by stirring.

33 grams, that is 25 percent by weight of the total sphere composition, of polymethylene polyphenylisocyanate, a reactive type with NCO content of 31.3 percent by weight, was added and intimately blended with the above mixture by means of a high speed stirrer. This formed the sphere-forming composition.

The aqueous phase comprised 100 grams of a sodium salt of styrene maleic anhydride dissolved in 5 liters of demineralized water. The sphere-forming composition was added slowly to the aqueous phase and stirred for 2 minutes with a high shear Waring blender. This produced an emulsion of spherical particles generally within the range 1-10 microns. The high shear blender was then replaced with a low speed stirrer, and the emulsion was stirred for a further 3 hours, during which time a polyurea surface layer was formed around the spherical particles by hydrolysis-initiated polymerization of the portion of the isocyanate at or near the surface of the spheres. During this time a reaction also commenced between the remainder of the isocyanate and the fatty acids of the safflower oil to form an acyl polyurea network throughout the particles.

The so formed dispersion was then filtered to remove practically all of the sodium styrene maleic anhydride, and the microspheres were resuspended in one liter of a 1 percent aqueous solution of the binder material polyvinyl alcohol. The dispersion was coated on a paper sheet to a dry coating weight of about 5 grams per square meter to form a back coating suitable for pressure manifold copying against an acidic front coating, as is well known in the art.

EXAMPLE 2

Example 1 was repeated, with the exception that the polyvinyl alcohol binder was replaced with sodium polyacrylate, which cross linked after the coating on paper was dried to become moisture insensitive.

EXAMPLES 3 AND 4

Examples 1 and 2 were repeated with the exception that the safflower oil was replaced with an equal weight of tung oil, to which was added cobalt naphthenate in a quantity equivalent to 0.1 gram metallic cobalt. The polymethylene polyphenylisocyanate content was reduced to 20 grams, that is 16.66 percent by weight of total sphere composition. The isocyanate reduction resulted in reduced surface layer thickness and lessened the acyl polyurea formation with the spheres; however the metallic drier assisted polymerization of the excess tung oil to form a matrix capable of maintaining the spherical shape of the particles by supporting the surface layer.

EXAMPLE 5

The insecticide S-1,2-di(ethoxyoarbonyl)ethyl 0,0-dimethyl phosphorodithioate (malathion) (55 grams), was dispersed with safflower oil (25 grams) after which polymethylene polyphenylisocyanate (20 grams) was added and blended by means of a high speed stirrer. The thus formed sphere composition was emulsified in 5 liter of a 1 percent aqueous solution of sodium lignin sulphonate by means of a high shear Waring blender as in Example 1.

The resultant dispersion was directly usable as an insecticide without further treatment.

EXAMPLE 6

Example 5 was repeated with the exception that malathion was replaced with an equal weight of diazinon, i.e. 0,0-diethyl 0-(2-isopropyl-4-methyl-6-pyrimidinyl) phosphorothioate.

EXAMPLE 7

Example 5 was repeated with the exception that malathion was replaced with an equal weight of the herbicide butylate (S-ethyl diisobutyldithiocarbamate).

EXAMPLE 8

Example 5 was repeated with the exception that malathion was replaced with an equal weight of copper naphthenate fungicide.

EXAMPLE 9

Perfume oil (40 grams), dibutyl phthalate (20 grams), and safflower oil (20 grams) were blended together, after which polymethylene polyphenylisocyanate (20 grams) was added and the mixture homogenized.

This sphere-forming composition was emulsified as in Example 1 and subsequently filtered to remove the emulsifier. Polyvinyl alcohol binder was added as in Example 1 to form a dispersion suitable for coating on to paper to produce perfumed paper. Perfume was released by rubbing the coated area of the paper.

EXAMPLE 10

The adhesive high molecular weight polyisobutylene resin (20 grams) admixed with low molecular weight liquid polyisobutylene resin (14 grams) was dispersed in 40 grams safflower oil. Polymethylene polyphenylisocyanate (20 grams) was added and the mixture homogenized.

This sphere-forming composition was emulsified as in Example 1 and subsequently filtered to remove the emulsifier. Polyvinyl alcohol binder was added as in Example 1 to form a dispersion suitable for spot coating on to paper to produce areas containing pressure sensitive adhesive.

EXAMPLE 11

Example 10 was repeated, with the exception that the polyisobutylene resin was replaced with styrene butadiene resin (50 grams), hydrogenated resin ester (25 grams), isoparaffinic hydrocarbon, boiling range 155°-177° C., (10 grams), and mineral oil (10 grams), and the safflower oil was replaced with an equal weight of tung oil. Polymethylene polyphenylisocyanate (20 grams) was added and the mixture homogenized.

The sphere-forming composition was emulsified as in Example 1, and subsequently filtered to remove the emulsifier. Polyvinyl alcohol binder was added as in Example 1 to form a dispersion suitable for spot coating onto paper to produce areas containing pressure sensitive adhesive. The tung oil substitution for the safflower oil caused the porous matrix to be somewhat more rigid than in Example 10; however, the presence of the isoparaffinic hydrocarbon solvent and mineral oil plasticizer allowed sufficient mobility of the adhesive fill material for satisfactory functioning as a pressure sensitive adhesive.

EXAMPLES 12-22

Each of Examples 1-11 was repeated with the exception that the polymethylene polyphenylisocyanate was replaced with an equal weight 4,4'-diphenylmethane diisocyanate and a catalytic quantity of triethylamine, such as 0.1 gram, was also added. Hydrolysis of the 4,4'-diphenylmethane diisocyanate occurred somewhat faster than did hydrolysis when polymethylene polyphenylisocyanate was used. However, the triethylamine catalyzed the acylurea formation with the vegetable oil to form the porous matrix at a rate compatible with the rate of formation of the polyurea surface layer.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. Method of preparing a spherical particle comprising:
   (1) admixing a releasable fill material, an isocyanate, and a matrix-forming co-reactant to form a mixture,
   (2) emulsifying said mixture in an aqueous medium containing a nonreactive emulsifying agent to provide a dispersion of spheres of said mixture,
   (3) hydrolyzing a first portion of the isocyanate near the surfaces of said spheres by contact with water in the aqueous medium to initiate formation of polyurea (a) at the surfaces of said spheres as a thin, substantially continuous layer and (b) in the interiors of the spheres as a continuum for some distance beneath the surfaces of said spheres, said continuum being a polyurea matrix, and reacting a second portion of the isocyanate within said spheres with said matrix-forming co-reactant to form additional matrix material in the interiors of said spheres.

2. The method of claim 1 comprising the additional step of removing said emulsifying agent from said dispersion.

3. The method of claim 2 comprising the additional step of removing the water from said dispersion.

4. The method of claim 2 wherein said emulsifying agent is removed from the dispersion by washing.

5. The method of claim 1 wherein the mixture in step 1 comprises from about 5% by weight to about 20% by weight matrix-forming co-reactant based on the weight of fill material.

6. The method of claim 1 wherein said matrix-forming co-reactant is a vegetable oil.

7. The method of claim 1 wherein said isocyanate is selected from the group consisting of aromatic polyfunctional isocyanates and aliphatic polyfunctional isocyanates.

8. A spherical particle comprising a thin, substantially continuous surface layer of polyurea, surrounding an interior portion comprising a matrix comprising polyurea, said matrix having releasable fill material contained therein, wherein said polyurea matrix forms a continuum extending from said continuous polyurea surface layer into the interior of said particle.

9. The particle of claim 8 wherein the releasable fill material is selected from the group consisting of insecticides, defoliants, fungicides, insect repellants, herbicides, dye percursors, dyes, perfume oils, and adhesives.

10. The particle of claim 8 wherein the diameter of said particle ranges up to about 1000 micrometers.

11. The particle of claim 8 wherein said matrix further comprises a second urea-containing polymer.

12. The particle of claim 11 wherein said second urea-containing polymer is an acylurea polymer.

* * * * *